(12) United States Patent
Medin et al.

(10) Patent No.: US 9,354,202 B2
(45) Date of Patent: May 31, 2016

(54) DETECTING MASS ON A MEMS BIOOSCILLATING RESONATOR ARRAY

(71) Applicants: David Lawrence Medin, Los Atlos, CA (US); James Michael Moniz, Groton, MA (US)

(72) Inventors: David Lawrence Medin, Los Atlos, CA (US); James Michael Moniz, Groton, MA (US)

( * ) Notice: Subject to any disclaimer, the term of this patent is extended or adjusted under 35 U.S.C. 154(b) by 772 days.

(21) Appl. No.: 13/624,694

(22) Filed: Sep. 21, 2012

(65) Prior Publication Data
US 2013/0068025 A1 Mar. 21, 2013

Related U.S. Application Data

(60) Provisional application No. 61/537,318, filed on Sep. 21, 2011.

(51) Int. Cl.
*G01N 29/00* (2006.01)
*G01N 29/02* (2006.01)
*G01N 29/036* (2006.01)

(52) U.S. Cl.
CPC ............ *G01N 29/022* (2013.01); *G01N 29/036* (2013.01); *G01N 2291/012* (2013.01); *G01N 2291/02466* (2013.01)

(58) Field of Classification Search
CPC ... G01N 29/022; G01N 29/12; G01N 29/036; G01N 29/22; G01N 29/24; G01N 29/32; G01N 29/36
USPC .............. 73/579, 580, 649, 657, 32 A, 24.06, 73/24.03, 23.3, 54.24, 54.26, 54.41, 61.75
See application file for complete search history.

(56) References Cited

U.S. PATENT DOCUMENTS

| | | | | |
|---|---|---|---|---|
| 5,837,885 A | * | 11/1998 | Goodbread | ............ B82Y 15/00 310/338 |
| 5,932,953 A | | 8/1999 | Drees et al. | |
| 6,111,342 A | * | 8/2000 | Muramatsu | .......... G01N 29/036 310/311 |
| 6,448,513 B1 | | 9/2002 | Kats et al. | |
| 6,557,416 B2 | * | 5/2003 | Chang | .................. G01N 29/036 73/23.3 |
| 7,036,375 B2 | * | 5/2006 | Nozaki | ..................... G01G 3/13 73/24.06 |

(Continued)

FOREIGN PATENT DOCUMENTS

| | | |
|---|---|---|
| EP | 1607725 A1 | 12/2005 |
| JP | 2002350218 A | 12/2002 |

OTHER PUBLICATIONS

Korean Examiner, AHN, Jae Yul, International Search Report and Written Opinion of the International Searching Authority, or the Declaration, International Application No. PCT/US2013/033168, mailed Jul. 1, 2013, 10 pages.

(Continued)

*Primary Examiner* — Helen Kwok
(74) *Attorney, Agent, or Firm* — Fish & Richardson P.C.

(57) ABSTRACT

A system configured to determine the mass of an object. The system generates a first output signal by transmitting an excitation signal through an oscillating resonator array. The oscillating resonator array includes a first oscillating resonator, a second oscillating resonator; and an electronic component coupled between the first oscillating resonator and the second oscillating resonator. A user adds an object to a surface of the oscillating resonator array. After adding the object, the system generates a second output signal by transmitting the excitation signal through the oscillating resonator array and determines a phase difference between the first output signal and the second output signal.

17 Claims, 6 Drawing Sheets

(56) References Cited

U.S. PATENT DOCUMENTS

| | | | | |
|---|---|---|---|---|
| 7,165,452 | B2* | 1/2007 | Kobayashi | G01G 3/16 73/580 |
| 7,216,543 | B2* | 5/2007 | Paik | G01G 3/13 73/32 A |
| 7,285,736 | B2 | 10/2007 | Korpi | |
| 7,814,795 | B2* | 10/2010 | Lee | G01G 3/13 73/54.24 |
| 8,409,875 | B2* | 4/2013 | Johal | G01N 33/54373 435/283.1 |
| 2005/0016276 | A1* | 1/2005 | Guan | G01N 29/022 73/579 |
| 2005/0087019 | A1* | 4/2005 | Face | G01N 29/14 73/649 |

OTHER PUBLICATIONS

W.H. King, Jr., "Piezoelectric sorption detector," Analytical Chemistry, vol. 36, No. 9, 1964, pp. 1735-1739.

Gaiter Sauerbrey "Verwendung von Schwingquarzen zur Wägung dünner Schichten und zur Mikrowägung", Zeitschrift für Physik vol. 155, No. 2, Apr. 1959, pp. 206-222.

Sauerbrey equation, 2013, retrieved from internet on Mar. 25, 2013 at http://en.wikipedia.org/wiki/Sauerbrey_equation, 2 pages.

\* cited by examiner

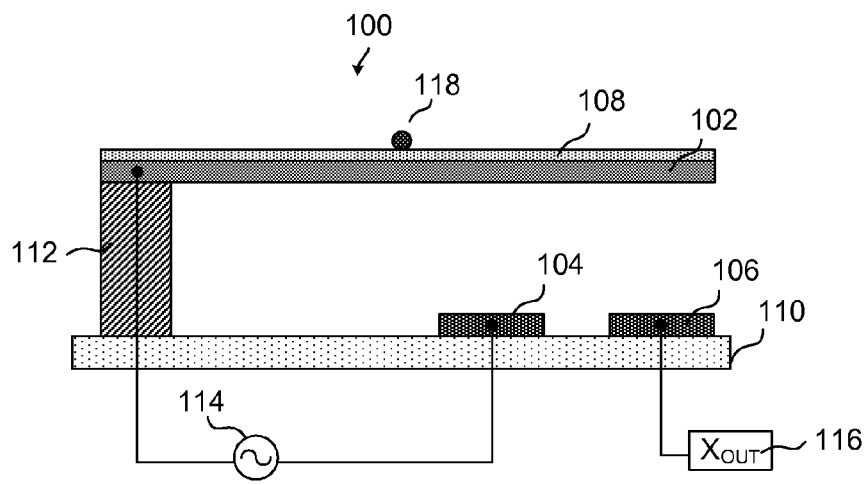
FIG. 1A
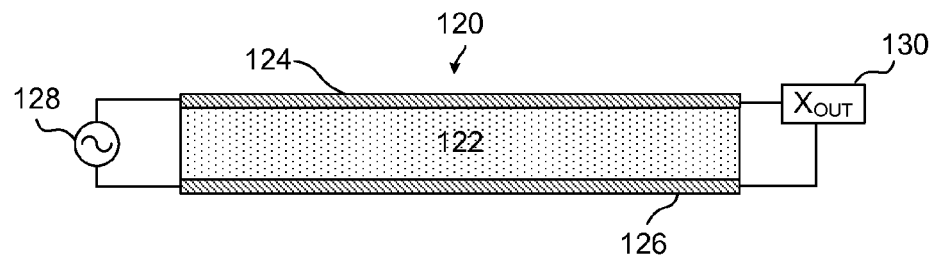
FIG. 1B
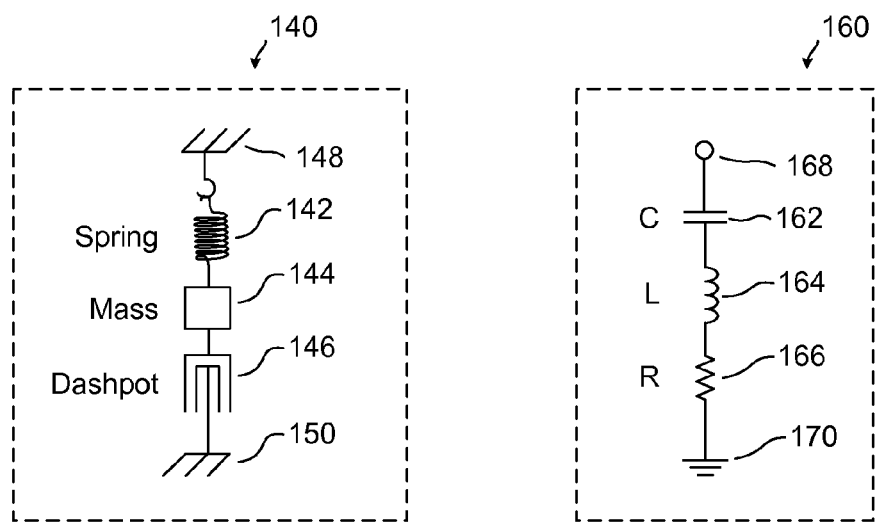
FIG. 1C
FIG. 1D

DETECTING MASS ON A MEMS BIOOSCILLATING RESONATOR ARRAY

CROSS-REFERENCE TO RELATED APPLICATIONS

This application claims the benefit and priority of U.S. Provisional Application Ser. No. 61/537,318, filed Sep. 21, 2011, the entire contents of which are hereby incorporated by reference.

TECHNICAL FIELD

This disclosure relates generally to electronics and more particularly to the measurement of the mass of chemical and biological compounds using oscillating resonator arrays.

BACKGROUND

A resonator can be used to measure mass by detecting the change in resonant frequency by the addition or removal of a small mass on the resonating surface. Resonators are useful, for example, in biological and chemical applications, including samples with a very small mass (e.g., <1 fg). The output of each of the resonators can be digitized using an analog to digital converter (ADC) and the resonant frequency can be determined by an amplitude peak or null.

The conventional approach for measuring chemical or biological samples using oscillating resonators can raise several problems, especially when measuring samples with very small masses. For example, one problem can be the increased measurement time. Long measurement times are undesirable for the user and can introduce errors due to biological (e.g. an ex-vivo sample can degrade or change in time), electrical, environment, material or mechanical changes. Another problem with the conventional approach can be noise. Signals with lower amplitude and higher frequency can be more susceptible to noise.

SUMMARY

A system including an oscillating resonator array can measure the change in phase, at one or more discrete frequencies or over a band of frequencies, as function of mass. The system generates a first output signal by transmitting an excitation signal through an oscillating resonator array. The oscillating resonator array includes a first oscillating resonator, a second oscillating resonator; and an electronic component coupled between the first oscillating resonator and the second oscillating resonator. A user adds an object to a surface of the oscillating resonator array. After adding the object, the system generates a second output signal by transmitting the excitation signal through the oscillating resonator array and determines a phase difference between the first output signal and the second output signal.

In some implementations, the oscillating resonator array has one or more resonance frequencies. In some implementations, the first oscillating resonator and second oscillating resonator are arranged in one of a series configuration and a parallel configuration. In some implementations, the electronic component includes one or more of: an active component, a passive component, a third resonator, and an amplifying component.

In some implementations, the first oscillating resonator is one of an electrostatic resonator, a force piezoelectric resonator, a mechanical resonator, a piezoelectric resonator, and an electrical resonator. In some implementations, the second oscillating resonator is one of an electrostatic resonator, a force piezoelectric resonator, a mechanical resonator, and an electrical resonator.

In some implementations, both the first and second oscillating resonators are coated with an attractor substance and exposing the second oscillating resonator, and not the first oscillating resonator, to material attracted to the attractor substance, thereby disposing the object onto the surface of the second oscillating resonator. In some implementations, the second oscillating resonator is coated with an attractor substance and exposing the first and second oscillating resonators to material attracted to the attractor substance, thereby disposing the object onto the surface of the second oscillating resonator. In some implementations, the first and second oscillating resonators are coated with different attractor substances and exposing both oscillating resonators to material attracted one of to the attractor substances, thereby disposing the object onto the surface of one the oscillating resonators. In some implementations, the object is a nucleic acid sample, deoxyribonucleic acid sample, a ribonucleic acid sample, a peptide nucleic acid sample, an antigen sample and an antibody sample. In some implementations, the object is an undesired substance, such as non-specific binding of an organic or inorganic matter on the surface. In some implementations, a measurement is taken before and after the object is added to the surface. In some implementations, the mass of the object is determined from the phase difference of two or more measurements. In some implementations, the identity of the object is determined from the location of the resonator surface corresponding to the phase difference. In some implementations, the concentration of a subset of the object is determined from the phase difference. In some implementations, the system sweeps the frequency of the excitation signal. In some implementations, the excitation signal has one or more discrete frequencies. In some implementations, the excitation signal is a periodic signal.

In some implementations, the difference of masses between a first object and a second object, is determined by generating a first output signal by transmitting an excitation signal through a first oscillating resonator array having a first surface with the first object disposed on the first surface, generating a second output signal by transmitting the excitation signal through a second oscillating resonator array having a second surface with the second object disposed on the second surface, and determining a phase difference between the first output signal and the second output signal. In some implementations, the first oscillating resonator array includes: a first resonator; a second resonator and a component affecting the impedance of a signal coupled between the first resonator and the second resonator. In some implementations, the second oscillating resonator array includes: a first resonator; a second resonator and a component affecting the impedance of a signal coupled between the first resonator and the second resonator. In some implementations, the first output signal and the second output signal are successively generated by switching a switch coupled between the first oscillating resonator array and the second oscillating resonator array from one position to another.

In some implementations, the system includes: a transmitter configured to generate an excitation signal, an oscillating resonator array circuit coupled to the transmitter and configured to receive the excitation signal, to generate a first output signal before adding the object to a surface of the oscillating resonator array circuit and to generate a second output signal after adding the object to the surface of the oscillating resonator array circuit and a detector coupled to the oscillating resonator array circuit and configured to determine a phase difference between the first output signal and the second output signal and to generate a mass detection signal based on the phase difference.

In some implementations, the system includes: a waveform generator configured to generate an excitation signal, a comparator bias voltage circuit configured to generate an analog reference signal and sweep the analog reference signal through a range of amplitudes, a comparator clock, an oscillating resonator array having the object disposed thereon, the oscillating resonator array being coupled to the waveform generator and configured to receive the excitation signal and generate an output signal, a comparator coupled to the oscillating resonator array and to the comparator bias voltage; and a latch circuit coupled to an output of the comparator and to the comparator clock, the latch being configured to capture a moment when the output of the comparator toggles because the analog reference signal becomes larger or smaller than the output signal of the oscillating resonator array and to generate a digital signal.

In some implementations, the system further includes an amplifying component coupled to the oscillating resonator array and to the comparator. In some implementations, the system further includes a memory to store the digital signal. In some implementations, the system further includes a processor coupled to the latch circuit, the processor being configured to determine an identity and a concentration of the object based on the digital signal.

Particular implementations of the oscillating resonator array can provide one or more of the following advantages. Objects with very small masses, such as nucleic acids, can be measured with high accuracy. The system can be adapted to accurately detect a particular mass magnitude by selecting the corresponding number of oscillating resonators to form the oscillating resonator array. The resonator array including components affecting the impedance of a signal coupled between adjacent resonators presents an additive or multiplicative effect as compared to one resonator on phase or multiple resonators, which allows the detection of mass by phase shift. The oscillating resonator array is compatible with a locally integrated ADC converter, which enhances the transmission of output signals to a memory. Numerous latches can share the same bias voltage source or can be offset from a source with bias threshold voltage thereby reducing cost, complexity and measurement variance. Numerous latches can be latched simultaneously or delayed from the same common latch signal, reducing wiring complexity and reducing potential measurement variances. High immunity to electrical noise can be achieved by placing the latch circuit in close proximity to the oscillating resonator array or the oscillating resonator array and using a digital output of the latch circuit. The system can be less susceptible to errors from biological, electrical, mechanical or environment changes due to simultaneous data capture performed by numerous latches. The digital outputs of the latched compactors can easily be multiplexed and/or combined into a digital signal through various means including the use of open drain or multiplexed outputs, which share the same wiring. The combined outputs of the comparators can be processed on the oscillating resonator array chip or transmitted to another chip or computer for processing.

It is appreciated that methods in accordance with the present disclosure can include any combination of the aspects and features described herein. That is, methods in accordance with the present disclosure are not limited to the combinations of aspects and features specifically described herein, but also include any combination of the aspects and features provided.

The details of one or more implementations of the present disclosure are set forth in the accompanying drawings and the description below. Other features and advantages of the present disclosure will be apparent from the description and drawings, and from the claims.

BRIEF DESCRIPTION OF THE DRAWINGS

FIGS. 1 A and B are diagrams of physical implementation of resonators such as electrostatic and piezoelectric resonators.

FIGS. 1 C and D are mechanical equivalent and electrical equivalent schematic diagrams of example oscillating resonators.

DETAILED DESCRIPTION

Example Oscillating Resonators

Figure 2A:
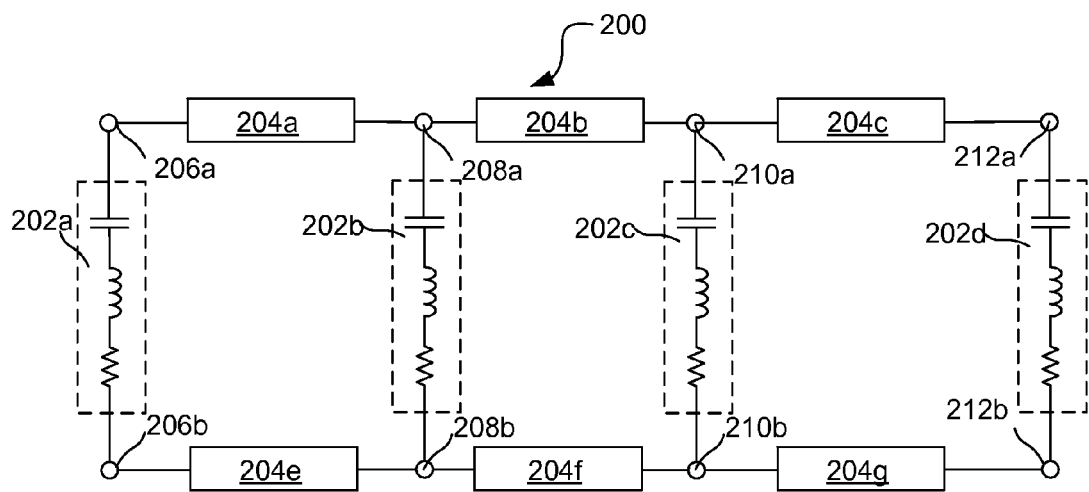
FIGS. 2 A, B and C are schematic diagrams of example oscillating resonator arrays.

FIGS. 1 A and 1B are diagrams of example oscillating resonators. FIG. 1A illustrates an example of an electrostatic resonator 100. The electrostatic resonator 100 includes electrodes 102, 104, 106. Electrode 102 is fixed on a structure 108 and electrodes 104 and 106 are fixed on a structure 110. The structure 108 and the structure 110 are each fixed at an end of an anchor 112. The electrostatic resonator 100 functions based on the electrostatic attraction force, created by a source 114, which applies a voltage potential between electrodes 102 and 104. The input voltage can be an alternating voltage, which induces an oscillation of the structure 108. The characteristics of the oscillation (e.g., amplitude, phase and frequency) can be measured between the electrodes 106 and 102 using a detector 116. By sweeping the input frequency with the source 114 and measuring the characteristics of the oscillation using the detector 116, the resonance of the electrostatic resonator 100 can be determined. The resonant frequency of the structure 108 can be lowered by adding an object 118 on the structure 108.

FIG. 1B illustrates an example of a piezoelectric resonator 120. The piezoelectric resonator 120 can be any type of piezoelectric resonator, such as a bulk acoustic wave resonator, a surface acoustic wave resonator, a film bulk acoustic resonator, a quartz crystal microbalance, etc. The piezoelectric resonator 120 includes a piezoelectric material (e.g., AlN, ZnO, PZT, quartz piezoelectric) 122 sandwiched between electrodes 124 and 126. Electrodes 124 and 126 can be excited by a source 128. The piezoelectric oscillation induced in the electrodes 124 and 126 can be measured with a detector 130. The oscillation frequency of the piezoelectric material 122 changes with the variation of the mass deposited on it.

FIG. 1C illustrates a mechanical equivalent schematic an example of a mechanical resonator 140. The mechanical resonator 140 includes a spring 142, a mass 144 and a dashpot 146. The mechanical resonator 140 can reversibly convert kinetic energy into potential energy. The oscillation induced in the mechanical resonator 140 can be measured with a detector at the connection point 148 or 50. The oscillation frequency of the mechanical resonator 140 changes with the variation of the mass 144.

FIG. 1D illustrates the electrical equivalent circuit model 160 of the mechanical resonator shown in FIG. 1C. The resonator's electrical equivalent circuit model 160 includes a capacitor 162, an inductor 164 and a resistor 166. The oscillation induced in resonator's electrical equivalent circuit model 160 can be measured with a detector between 168 and 170. The oscillation frequency of the resonator's electrical equivalent circuit model 160 changes with the variation of the capacity of the capacitor 162 or the inductance of the inductor 164. By adding a mass to resonator's electrical equivalent circuit model 160, the resonant frequency of the electrical resonator 160 can be modified.

Using the resonance frequency, any of the described oscillating resonators or any other type of oscillating resonators can be configured to determine the value of the mass added to the oscillating resonator. By way of non-limiting example, the object disposed on the oscillating resonator (e.g., 100 in FIG. 1A, 120 in FIG. 1B, 140 in FIG. 1C or 160 in FIG. 1D) can be a sample including multiple molecules (e.g. nucleic acids, proteins, deoxyribonucleic acid sample, a ribonucleic acid sample, peptide nucleic acid sample, antigen sample and antibody sample), each molecule having a particular mass. In some implementations, the oscillating resonator (e.g. 100 in FIG. 1A, 120 in FIG. 1B, 140 in FIG. 1C or 160 in FIG. 1D) can be coated with an attractor substance to preferentially target particular molecules of the sample, thereby disposing only the targeted molecules onto the surface of the oscillating resonator. For example, preferential targeting can be established though hybridization of target nucleic acids that with complementary probes that are bound to the surface of the oscillating resonator.

In some implementations, the oscillating resonator (e.g. 100 in FIG. 1A, 120 in FIG. 1B, 140 in FIG. 1C or 160 in FIG. 1D) can be loaded with multiple objects. For example, the surface of the oscillating resonator (e.g. 100 in FIG. 1A, 120 in FIG. 1B, 140 in FIG. 1C or 160 in FIG. 1D) can be coated to attract nonspecific nucleic acids binding proteins. In the context of the provided example, the oscillating resonator (e.g. 100 in FIG. 1A, 120 in FIG. 1B, 140 in FIG. 1C or 160 in FIG. 1D) is first loaded with nonspecific nucleic acids-binding proteins and second nucleic acids are added.

In some implementations, the resonant frequency of the oscillating resonator can be measured both before and after adding an object. The measured difference in resonating amplitude, phase and/or frequency can be used to determine the change in mass. In some implementations, the output signal characteristics of the oscillating resonator can be measured at multiple time or frequency points after adding particular sample types (e.g., targeted molecules) to the oscillating resonator. The difference in output signal characteristics at one or more frequencies near the resonant frequency can be used to determine the change in mass corresponding to a particular type of molecule. In some implementations, as further described with reference to FIGS. 3, 4 and 5, the output signal of multiple resonators with different types of samples can be simultaneously measured to determine the change in resonant frequency or phase as function of mass In some implementations, the accuracy of the detection of the change in mass as function of the change in frequency or phase can be improved by coupling multiple oscillating resonators in particular configurations, as described in further detail with reference to FIG. 2.

Example Oscillating Resonator Arrays

Figure 2B:
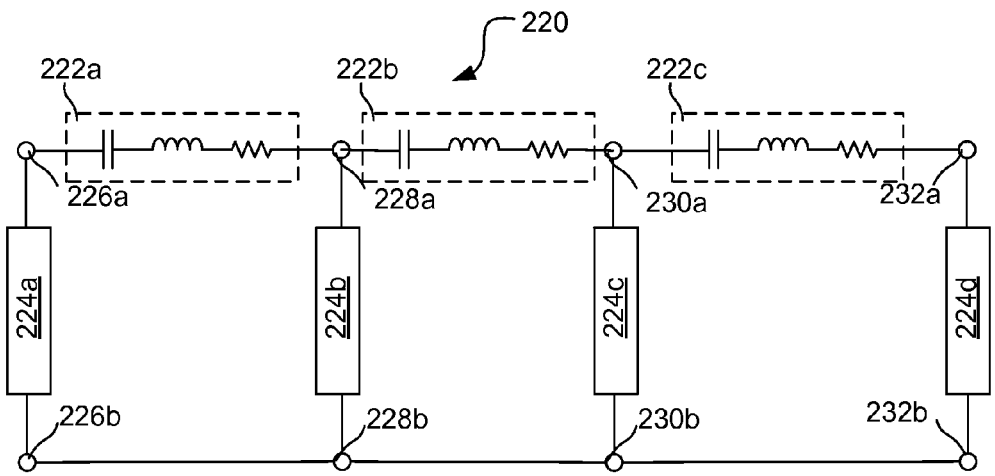
Figure 2C:
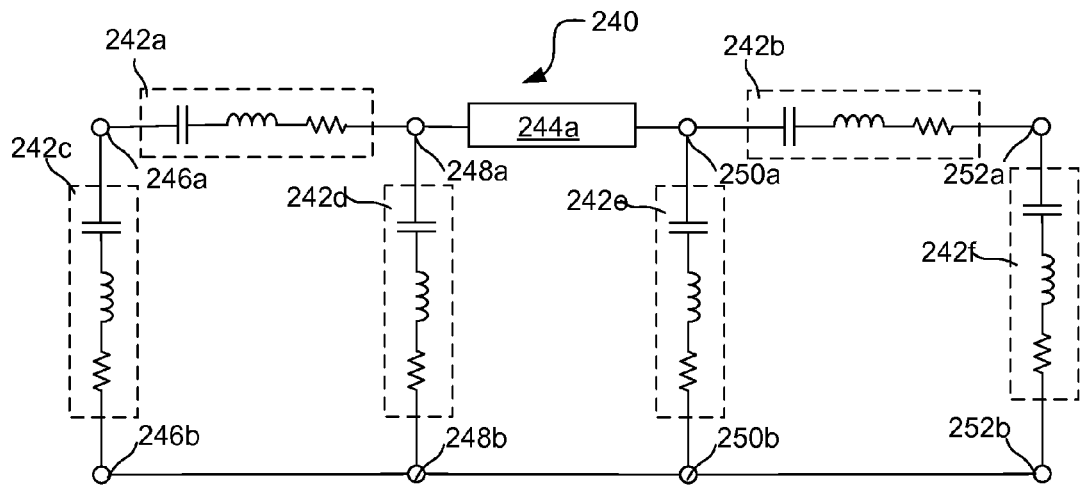

FIGS. 2A, B and C are schematic diagrams of an example oscillating resonator arrays 200, 220 and 240 in FIG. 2A, 220 in FIGS. 2B and 240 in FIG. 2C. The oscillating resonator arrays 200, 220 and 240 include multiple oscillating resonators (e.g. 202a, 202b, 202c and 202d) and multiple electronic components (e.g. passive or active electronic components).

By way of non-limiting example, each oscillating resonator is illustrated in FIGS. 2A, B and C as an electrical equivalent schematic of a resonator. However, according to implementations of the current disclosure, any type of oscillating resonator (including the types described in detail with reference to FIGS. 1A, B, C and D) can be used as oscillating resonators in the configurations described herein.

The number of the oscillating resonators included in an oscillating resonator array can be varied to improve the accuracy and dynamic range of the mass detection for a particular order of magnitude. For example, the number of the oscillating resonators included in an oscillating resonator array can be increased to improve the measurement of smaller masses and to enable a wider range of masses to be measured.

In some implementations, all of the oscillating resonators in an oscillating resonator array have the same resonant frequency. In some other implementations, the oscillating resonators have different resonating frequencies. In some implementations, objects with equal masses are added to all oscillating resonators. In some implementations, objects with different masses are added to the oscillating resonators.

FIG. 2A illustrates an example oscillating resonator array 200 including multiple oscillating resonators (202a, 202b, 202c and 202d) arranged in a ladder configuration. The oscillating resonators 202a, 202b, 202c and 202d are connected in a parallel configuration. One or more electronic components (e.g., 204a, 204b, 204c, 204d, 204e and 204f) can be coupled between the oscillating resonators 202a, 202b, 202c and 202d. In some implementations the electrical components are, e.g., passive or amplifying components or even other oscillating resonators. In some implementations, one or more of the connection points is an electrical ground node.

In some implementations, the connection points 206a and 206b are connected to a source (e.g. a frequency generator). In some implementations, each of the pairs of connection points 208a and 208b, 210a and 210b, 212a and 212b are connected to a detector (e.g. phase detector). In some implementations, only the connection points of an oscillating resonator last in a chain of oscillating resonators (212a and 212b) are connected to the detector.

FIG. 2B illustrates an example oscillating resonator array 220 including multiple oscillating resonators (222a, 222b and 222c) arranged in a lattice configuration. The oscillating resonators 222a, 222b and 222c are connected in series. One or more electronic components (e.g., 224a, 224b, 224c and 224d) can be coupled between the oscillating resonators 222a, 222b and 222c.

In some implementations, the connection points 226a and 226b are connected to a source (e.g., a frequency generator). In some implementations, each of the pairs of connection points 228a and 228b, 230a and 230b, 232a and 232b are connected to a detector (e.g., phase detector). In some implementations, only the connection points of an oscillating resonator last in a chain of oscillating resonators (232a and 232b) are connected to the detector. FIGS. 2A and B are examples of possible circuit topologies and configurations of multi-resonator circuits for mass detection. Some other examples are single ended and differential, 2-port, 3-port, and n-port configurations, ladder, stacked, and lattice topologies.

FIG. 2C illustrates an example oscillating resonator array 240 including multiple oscillating resonators (242*a*, 242*b*, 242*c*, 242*d* and 242*e*) arranged in a ladder configuration. Two of the oscillating resonators 242*a* and 242*b* are connected in series. Three of the oscillating resonators 242*c*, 242*d*, 242*e* and 242*f* are connected in a parallel configuration. One or more electronic components (e.g., 244*a*) can be coupled between the oscillating resonators 242*a* and 242*b* and can be used to amplify the signal between two or more resonators.

In some implementations, the connection points 246*a* and 246*b* are connected to a source (e.g., a frequency generator). In some implementations, each of the pairs of connection points 248*a* and 248*b*, 250*a* and 250*b*, 252*a* and 252*b* are connected to a detector (e.g., phase detector). In some implementations, only the connection points of an oscillating resonator last in a chain of oscillating resonators (252*a* and 252*b*) are connected to the detector.

Example Circuit for Detection of Mass Change

Figure 3:
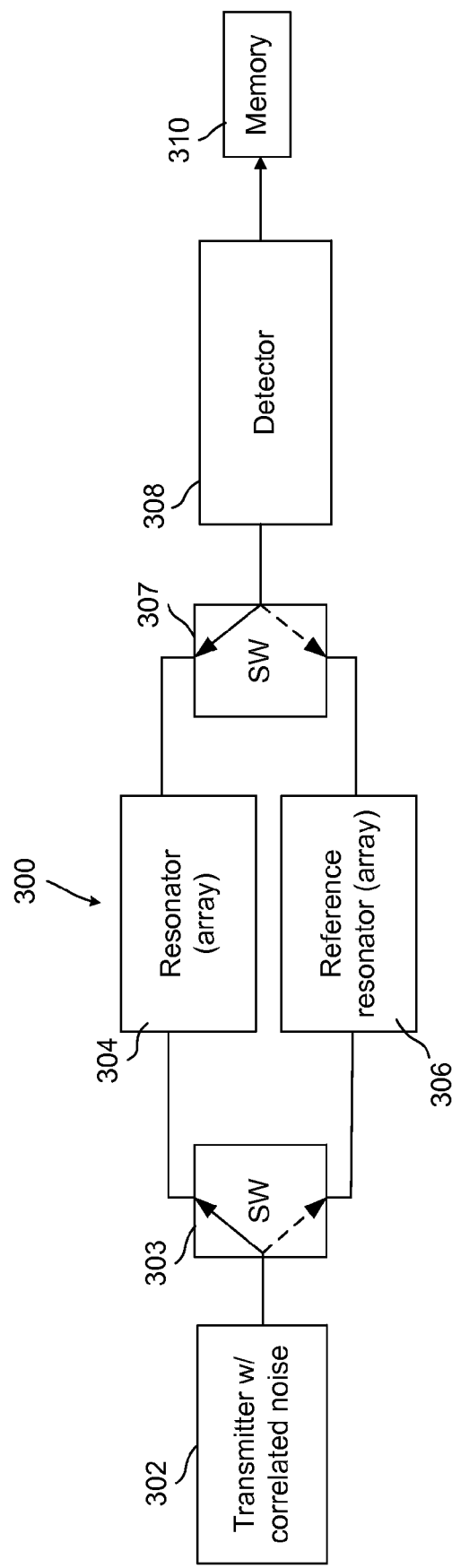
FIG. 3 is a schematic diagram of an example circuit including oscillating resonator arrays configured to detect the change with mass.

FIG. 3 is an example circuit 300 for detecting the mass change. In some implementations, the example circuit 300 can include a transmitter 302, a switch 303, a first oscillating resonator array 304, a second oscillating resonator array 306, a switch 307, a detector 308 and a memory 310. Each of the oscillating resonator arrays can include one or more oscillating resonators. For example, the oscillating resonator arrays 304 and 306 can be any type of oscillating resonators (e.g. 100 in FIG. 1A, 120 in FIG. 1B, 140 in FIGS. 1C and 160 in FIG. 1D). Each oscillating resonator array 304 and 306 is configured as a two port system as shown in FIG. 3.

In some implementations, the first oscillating resonator array 304 has an object with a particular mass disposed on a surface of the oscillating resonator array, so that the mass of the object can be determined. The second oscillating resonator array 306 in the circuit 300 does not include any additional object, representing a reference resonator array. In some implementations, each oscillating resonator array 304 and 306 individually includes an object with a particular mass (different from each other). For example, the oscillating resonator array 306 can include an object with a known mass or a known output signal. The oscillating resonator array 306 with the known mass works as a reference resonator array.

In some implementations, the response of the first oscillating resonator array 304 and second oscillating resonator array 306 to the same signal source is successively measured before and after an object with a particular mass was disposed on the surface of the oscillating resonator array 304.

The same signal source, with known amplitude and phase characteristics, can be successively applied through the switch 303 to both the oscillating resonator array 304 and the reference oscillating resonator array 306. As shown in FIG. 3, the switch 303 has two positions, one to direct the signal to the oscillating resonator array 304 and another one to direct the signal to the reference oscillating resonator array 306. The output of the oscillating resonator arrays 304 and 306 is transmitted over the switch 307 to the detector 308. The output signals are successively transmitted by changing the switch 307 from one position to another, corresponding to the position of the switch 303. In some implementations, the switches 303 and 307 are matrix switchers. In some implementations, the switches 303 and 307 have the same impedance as the oscillating resonator arrays 304 and 306.

The corresponding changes in amplitude and phase are successively detected by the detector 308. The detector 308 can be a phase detector. For example, the phase detector can be a frequency mixer, an analog multiplier or a logic circuit that generates a voltage signal, which represents the difference in phase between the two signals generated by the oscillating resonator (arrays) 304 and 306.

In some implementations, the phase response produced by the oscillating resonator array 304 loaded with the mass is monotonic and approximates a linear equation near the resonant frequency. As such, the phase curve can be determined with high accuracy even if the oscillating resonator array 304 has a low quality factor and the signal contains noise. The monotonicity of the signal generated by the oscillating resonator array 304 allows multiple data points to be used. The linearity of the curve allows curve fitting and various signal processing methods to be employed to determine the resonant frequency of the resonator with high resolution. In some implementations, the output of the detector 308 can be stored in an internal or external memory.

Example Circuit with a Comparator Bias Voltage

Figure 4:
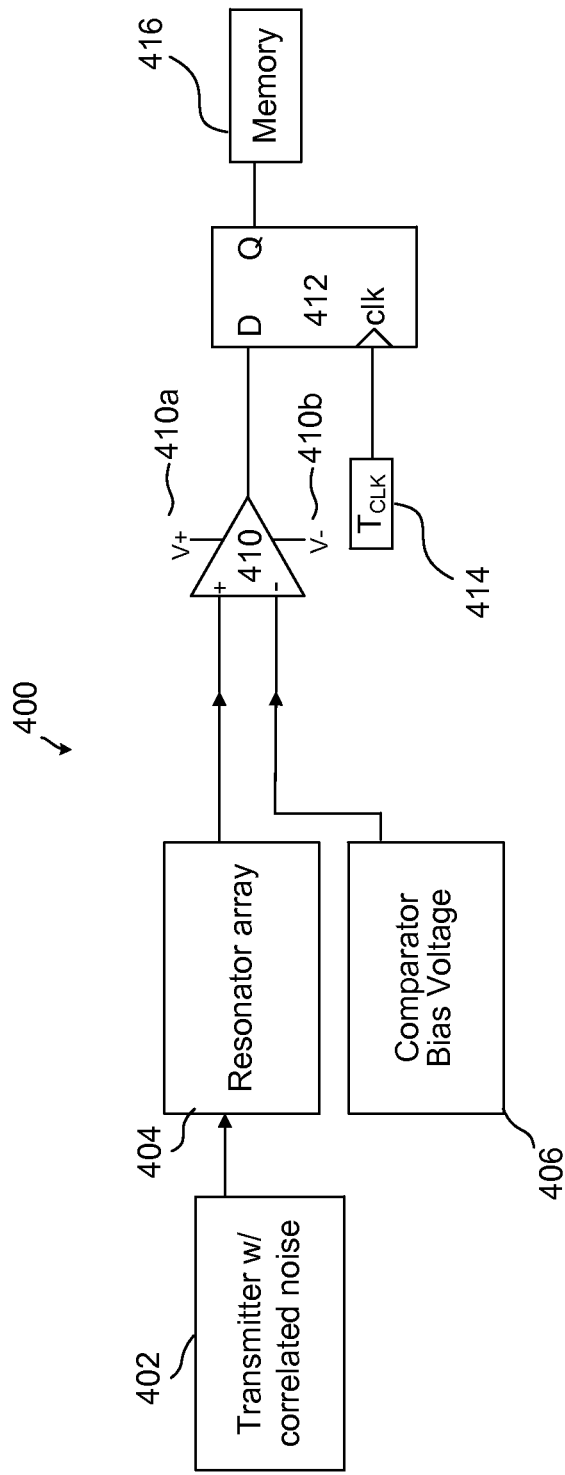
FIG. 4 is a schematic diagram of an example circuit with a comparator bias voltage.

FIG. 4 is a schematic diagram of an example of a circuit 400 including a comparator bias voltage. In some implementations, the circuit 400 can include a transmitter 402, an oscillating resonator array 404, a comparator bias voltage 406, a comparator 408, a latch 410 and a clock 412 and a memory 414. The oscillating resonator array can include one or more oscillating resonators.

The oscillating resonator array 404 is loaded with an object having an unknown mass, which can be determined with the circuit 400. The oscillating resonator array 404 is configured as a two port system as shown in FIG. 4. The oscillating resonator array 404 receives as input a signal generated by the transmitter 402. In some implementations, the resonating excitation input for the oscillating resonator array 404 is a known electrical signal. In some implementations, the transmitter 402 generates complex modulated signals. In some implementations, the transmitter 402 generates a single frequency signal with a known amplitude and phase. The frequency of the signal generated by the transmitter 402 can be swept over time from a frequency known to be lower than the lowest possible resonant frequency of the oscillating resonator array 404 to a frequency known to be higher than the highest resonant frequency of the oscillating resonator array 404. The oscillating resonator array 404 generates a signal with unknown frequency and phase, the signal characteristics being dependent on the mass of the object loaded on the oscillating resonator array 404.

The comparator bias voltage 406 sweeps over a particular range of frequencies, covering the resonance frequency of the oscillating resonator array 404. The comparator bias voltage 406 generates a reference signal with known characteristics (e.g., frequency and phase). The signal generated by the oscillating resonator array 404 and the signal generated by the comparator bias voltage 406 are used as differential input for the comparator 408.

In some implementations, the circuit 400 includes a comparator 408 to digitize the output of the resonator or resonator array 404. In some implementations, the comparator 408 can be an operational amplifying component. The comparator 408 has two inputs, inverting and non-inverting and an output. One input signal is the analog output, or modified analog output of the oscillating resonator array 404 and the other signal is a reference signal with variable magnitude generated by the comparator bias voltage 406. The comparator 408 can include two power supply pins (V+ 410a and V− 410b). The function of the two power supply pins (V+ 410a and V− 410b) is to provide additional power for the amplification of the output signal. The comparator 408 can operate in a non-linear fashion, comparing the voltages of the two inputs and providing a binary logic output voltage. These two states can represent the sign of the voltage difference between the two inputs. In some implementations, the output of the comparator is a binary output (e.g. 0 and 1), to indicate if the signals are equal or different. For example, if the voltage of the non-inverting comparator input is greater that the voltage of the inverting input, the comparator output will be a logic "1". Alternatively, if the voltage of the non-inverting comparator input is less that the voltage on the inverting input, the comparator output will be a logic "0". The reference input, received from the comparator bias voltage 406 can be used as the threshold voltage of signal input, at which the comparator 408 switches the output from a low voltage signal to a high voltage signal. The threshold voltage of the comparator 408 can be changed using a variable voltage source, referred to as a bias voltage. In some implementations, the bias voltage is varied with sufficient resolution and the amplitude of the input voltage is determined within a desired voltage range.

The amplitude of the input signal received from the oscillating resonator array 404 can also be varied to increase the resolution in determining the efficiency of the resonator at a given frequency. In some implementations, the amplitude of the input signal received from the oscillating resonator array 404 is varied with sufficient accuracy and the comparator 408 is used with a single threshold voltage. In some implementations, the comparator 408 produces an output signal that can be hundreds of thousands of times larger than the difference between its input signals. In some implementations, the output signal generated by the comparator 408 can be a square signal. In some implementations, the comparator 408 is physically small and can therefore be placed in close proximity to the resonator.

In some implementations, a variable gain amplifying component is placed between the oscillating resonator array 404 and the comparator 408 (not illustrated in FIG. 4). Changing the gain of the variable gain amplifying component has a similar effect to changing the bias voltage of the comparator bias voltage 406. For example, the output of the comparator bias voltage 406 can be a fixed voltage. In some implementations, both the variable gain amplifying component signal and the bias voltage of the comparator bias voltage 406 can be varied.

The comparator 408 transmits the output signal to the latch 410. In some implementations, the latch 410 also receives input from a clock 412. The latch 410 can be configured to combine the input from the comparator 408 and the clock 412 to convert the signal received from the comparator 408 into a digital signal. In some implementations, the output of the latch is transmitted to a memory 414 for storage.

In some implementations, the input frequency of the oscillating resonator array 404 and the output frequency of the oscillating resonator array 404 are correlated to determine minimum loss (e.g. maximum amplitude) and the resonant frequency (e.g. distinctive phase shift of the output signal). For an oscillating resonator array having anti-resonant characteristics or other circuit connections (e.g. piezoelectric configurations or shunt circuit resonators), the minimum amplitude and a distinctive phase shift of the output signal of the oscillating resonator array are determined to identify the shunt resonant frequency.

Example Circuit with Analog to Digital Conversion Using Comparators

Figure 5:
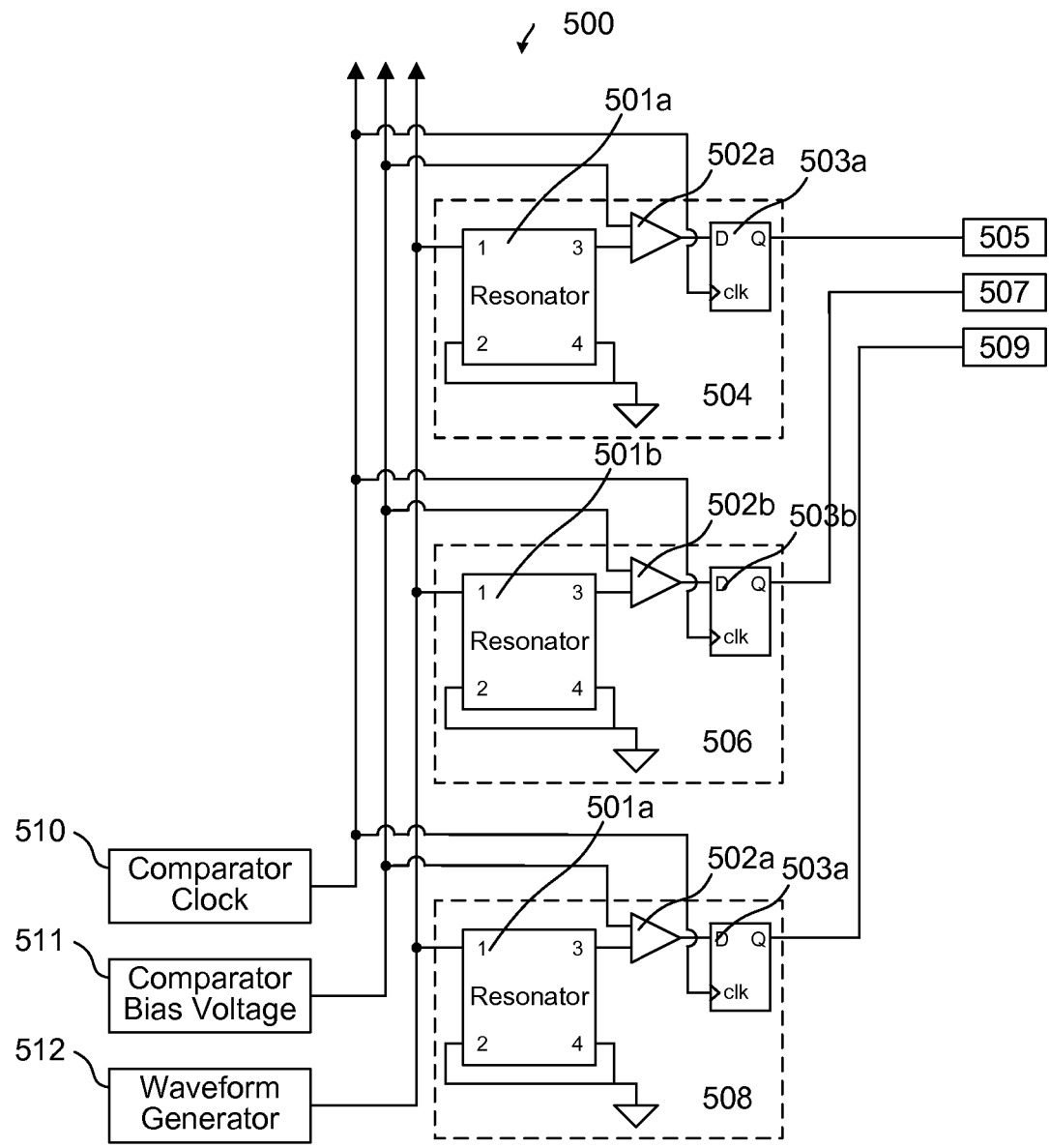
FIG. 5 is a schematic diagram of an example circuit including an analog memory.

FIG. 5 is a schematic diagram of an example circuit 500 configured to perform analog to digital conversion using comparators. The circuit 500 can include multiple (two or more) oscillating resonator (arrays) 501a, 501b and 501c, a corresponding number of comparators 502a, 502b and 502c, a corresponding number of latch circuits 503a, 503b and 503c, a corresponding number of analog memories 505, 507 and 509, a comparator clock 510, a comparator bias voltage circuit 511 and a waveform generator 512.

The waveform generator 512 transmits the predetermined excitation signal to each oscillating resonator array 501a, 501b and 501c. The comparator bias voltage circuit 511 is configured to sweep through a range of digital output values and convert those digital output values to analog signals, generating analog reference signals. The comparator bias voltage circuit 511 transmits the analog reference signals to each comparator 502a, 502b and 502c.

Each oscillating resonator array 501a, 501b and 501c is coupled to the waveform generator. In some implementations, each oscillating resonator array 501a, 501b and 501c has an object with an unknown mass, which can be determined using the circuit 500. In some implementations, the objects added to each oscillating resonator array 501a, 501b and 501c have equal masses. In some implementations, the objects added to each oscillating resonator array 501a, 501b and 501c have different masses. In some implementations, the measurements performed with the circuit 500 are repeated after adding one or more objects with equal or different masses on one or more oscillating resonator arrays. Each oscillating resonator array 501a, 501b and 501c is configured to receive the predetermined excitation signal and to generate an output signal. Each oscillating resonator array 501a, 501b and 501c transmits the output signal to a corresponding comparator 502a, 502b and 502c, respectively.

In some implementations, the amplifying components 502a, 502b and 502c can be comparators, as described with reference to FIG. 4. All amplifying components 502a, 502b and 502c receive input from the corresponding oscillating resonator array 501a, 501b and 501c and the comparator bias voltage. Each comparator 502a, 502b and 502c provides output for the corresponding latch circuit 503a, 503b and 503c, respectively.

In some implementations, the comparator bias voltage circuit 511 starts sweeping through a particular range transmitting periodic signals. At a particular point in the range, the output of the comparator bias voltage circuit 511 is greater than the output of the oscillating resonator array 501a, 501b and 501c, and the corresponding comparator 502a, 502b and 502c flips. The corresponding latch circuit 503a, 503b and 503c captures the flip. Since the output of the comparator bias voltage circuit 511 at the flip point is known, the voltage produced by the oscillating resonator array 501a, 501b and 501c can be identified.

In some implementations, each latch circuit 503a, 503b and 503c is configured to determine a phase difference between the output signal generated by the corresponding comparator 502a, 502b and 502c and the reference signal. In some implementations, a processor is coupled to each latch circuit 503a, 503b and 503c. The processor can be configured to determine an identity and a concentration of the object added to the corresponding oscillating resonator array 501a, 501b and 501c based on the analog signal.

In some implementations, the output of each oscillating resonator array 501a, 501b and 501c is buffered and used to continuously charge a capacitor. The capacitor can average the voltage output of the oscillating resonator array 501a, 501b and 501c over time. At the desired time, a switch can be closed and the average voltage can be measured by an averaging circuit. The averaging circuit can be a filter, a charge pump, or other analog memory circuit. The average signal can be latched by the corresponding latch circuit 503a, 503b and 503c. The switch can be implemented in various locations in the circuit 500. In some implementations, the circuit 500 does not use any switch.

In some implementations, multiple analog memory signals can be routed to multiplexed comparators or ADCs. In some implementations, two or more analog memory outputs can be summed for parallel processing.

The bias voltage to the comparators can be created with a digital to analog converter, a charge pump, a DC-DC converter or other known methods. Numerous oscillating resonator array comparators can share the same bias voltage source. Numerous oscillating resonator arrays can be offset from a source with bias threshold voltage. Numerous oscillating resonator array comparators can be latched simultaneously or delayed from the same common latch signal. The digital outputs of the compactors can easily be multiplexed and/or combined into a digital signal through various means including the use of open drain or multiplexed outputs to allow numerous comparators to share the same wiring. The combined outputs of the comparators can be processed on the oscillating resonator array chip or transmitted to another chip for processing.

In some implementations, the input of each oscillating resonator array 501a, 501b and 501c can be connected to the output of a corresponding sustaining comparator 502a, 502b and 502c, to sample the output of the sustaining comparator 502a, 502b and 502c. The bias voltage to set the latch circuit 503a, 503b and 503c threshold can be created with a digital to analog converter, a charge pump, a DC-DC converter or other methods.

Numerous latch circuits 503a, 503b and 503c can share the same bias voltage source. Numerous comparators 502a, 502b and 502c can be latched simultaneously or delayed from the same common latch signal, reducing wiring complexity and reducing potential measurement variances. The digital outputs of the comparators can be multiplexed and/or combined into a digital signal through various means including the use of open drain or multiplexed outputs to allow numerous comparators to share the same wiring. The combined outputs of the comparators can be processed on the oscillating resonator array chip or transmitted to another chip for processing.

In some implementations, numerous latch circuits 503a, 503b and 503c share the same bias voltage source or can be offset from a source with bias threshold voltage. In some implementations, the latch circuit 503a, 503b and 503c can be designed with a predetermined threshold voltage based on the expected amplifying component output signal or oscillating resonator array output signal characteristics. For example, by AC coupling the output signal of an oscillating resonator array (e.g. 501a, 501b or 501c) and constructing a latch circuit 503a, 503b and 503c with a threshold voltage of 0V, the circuit 500 functions as a zero crossing detector. When the circuit 500 functions as a zero crossing detector it may not be necessary to adjust the voltage threshold of the latch circuit 503a, 503b and 503c once the device is constructed. The latch circuit 503a, 503b and 503c can be used to count the number of zero crossings over a period to determine the frequency of an oscillator. If two or more oscillators are used, the count can represent the difference in frequency of the oscillating resonator (arrays) 501a, 501b or 501c. In some implementations, the oscillating resonator (arrays) 501a, 501b or 501c are constructed to react similarly to changes in environmental factors (e.g., temperature, voltage and noise), enabling effective cancellation of the measurement errors due to the environmental factors.

Example Flowchart

Figure 6:
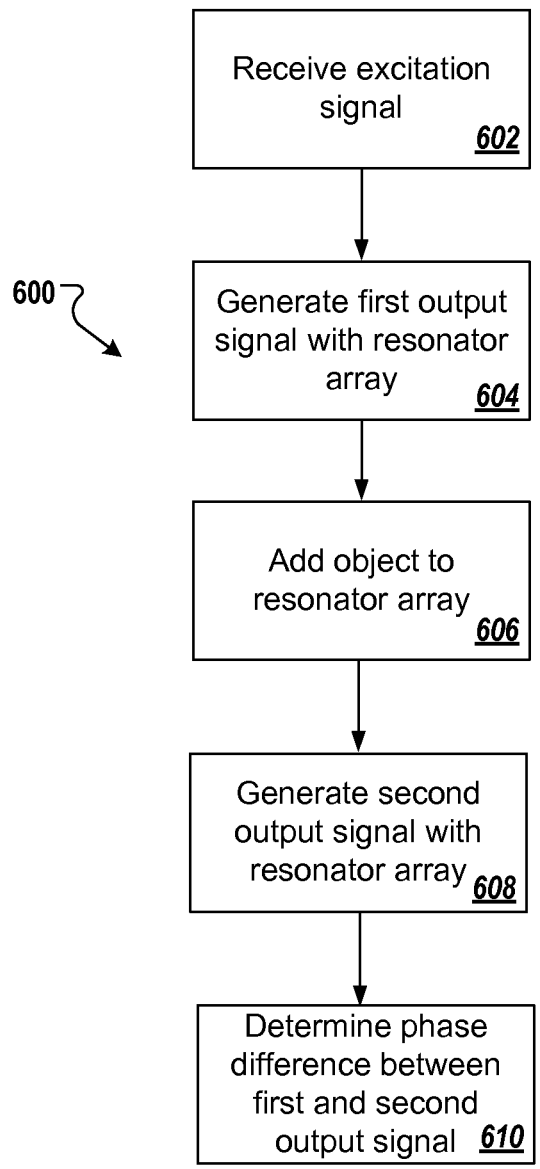
FIG. 6 is a flowchart depicting an example process that can be executed in accordance with implementations of the present disclosure.

FIG. 6 is a flowchart depicting an example process 600 that can be executed in accordance with implementations of the present disclosure. In some examples, the example process 600 can include operations that are performed by a user of the system or by one or more electronic components of the circuits described with reference to FIGS. 3-5. The example process 600 is an example mass detection protocol with output that can be stored in an internal or external memory.

An excitation signal is received by an oscillating resonator array 602. The oscillating resonator array can be a 2-port or more than 2-port circuit. The oscillating resonator array can include one or more oscillating resonators and an electronic component coupled between the resonators (e.g., as described with reference to FIG. 2).

The oscillating resonator array generates a first output signal 604. In some implementations, the oscillating resonator array can have one or more known resonances. In some implementations, the output signal generated by the oscillating resonator array can be used as a reference signal.

A user of the system adds an object to the oscillating resonator array 606. For example, the object added to the oscillating resonator array can be a nucleic acid sample. The oscillating resonator array receives an excitation signal identical with the initial excitation signal and generates a second output signal 608. When a mass is loaded on the oscillating resonator array, a distinct amplitude and phase shift appears at the known resonances.

The phase difference between the first output signal and the second output signal can be determined 610. For example, the first and the second output signals can be compared using the amplitude and phase detector circuits discussed with reference to FIGS. 3-5.

What is claimed is:

1. A system for determining a mass of an object, the system comprising:
    a waveform generator configured to generate an excitation signal;
    a comparator bias voltage circuit configured to generate an analog reference signal and sweep the analog reference signal through a range of amplitudes;
    a comparator clock;
    an oscillating resonator array having the object disposed thereon, the oscillating resonator array being be coated with an attractor substance to preferentially target particular molecules of the object, being coupled to the waveform generator and being configured to receive the excitation signal and generate an output signal;
    a comparator coupled to the oscillating resonator array and to the comparator bias voltage circuit; and
    a latch circuit coupled to an output of the comparator and to the comparator clock, the latch circuit being configured to capture a moment when the output of the comparator toggles because the analog reference signal becomes larger or smaller than the output signal of the oscillating resonator array and to generate a digital signal.

2. The system of claim 1, further comprising an amplifying component coupled to the oscillating resonator array and to the comparator.

3. The system of claim 1, further comprising a memory to store the digital signal.

4. The system of claim 1, further comprising a processor coupled to the latch circuit, the processor being configured to determine an identity and a concentration of the object based on the digital signal.

5. The system of claim 1, wherein the oscillating resonator array comprises a first oscillating resonator and a second oscillating resonator arranged in one of a series configuration, a parallel configuration and a mixed configuration.

6. The system of claim 1, wherein the oscillating resonator array comprises one or more of: an active component, a passive component, a third resonator, an impedance altering component and an amplifying component.

7. The system of claim 1, wherein the oscillating resonator array comprises one of an electrostatic resonator, a force piezoelectric resonator, a mechanical resonator, an electrical resonator and a piezoelectric resonator.

8. The system of claim 1, wherein the oscillating resonator array exhibits resonance for a narrow range of frequencies.

9. The system of claim 1, wherein the excitation signal comprises one of an electrostatic field, a charge, a magnetic field, an electromagnetic field and a mechanical impulse.

10. The system of claim 1, wherein the object is a nucleic acid.

11. The system of claim 10, wherein the nucleic acid is one of a deoxyribonucleic acid sample, a ribonucleic acid sample, a peptide nucleic acid sample, an antigen sample and an antibody sample.

12. The system of claim 1, wherein the object is a substance not specifically bound to the surface of the oscillating resonator array.

13. The system of claim 1, wherein the object is a substance specifically bound to the surface of the oscillating resonator array.

14. The system of claim 1, wherein the latch circuit is configured to capture the moment before and after the object is added to the oscillating resonator array.

15. The system of claim 1, further comprising one or more processors configured to determine an identity of the object from the digital signal.

16. The system of claim 15, wherein the one or more processors are configured to determine a concentration of a subset of the object from the digital signal.

17. The system of claim 1, wherein the excitation signal is a periodic signal.

* * * * *